(12) United States Patent
Lindsay et al.

(10) Patent No.: US 9,102,656 B2
(45) Date of Patent: Aug. 11, 2015

(54) USE OF ROSUVASTATIN LACTOLS AS MEDICAMENTS

(71) Applicant: RedX Pharma Limited, Manchester (GB)

(72) Inventors: Derek Lindsay, Manchester (GB); Peter Jackson, Manchester (GB)

(73) Assignee: RedX Pharma Limited, Manchester (GB)

( * ) Notice: Subject to any disclaimer, the term of this patent is extended or adjusted under 35 U.S.C. 154(b) by 0 days.

(21) Appl. No.: 14/029,056

(22) Filed: Sep. 17, 2013

(65) Prior Publication Data
US 2014/0018381 A1    Jan. 16, 2014

Related U.S. Application Data

(62) Division of application No. 13/255,705, filed as application No. PCT/GB2010/050409 on Mar. 10, 2010, now abandoned.

(30) Foreign Application Priority Data

Mar. 10, 2009    (GB) .................................. 0904100.5

(51) Int. Cl.
C07D 405/06    (2006.01)
A61K 31/505    (2006.01)
C07D 405/14    (2006.01)

(52) U.S. Cl.
CPC ............ *C07D 405/06* (2013.01); *A61K 31/505* (2013.01); *C07D 405/14* (2013.01)

(58) Field of Classification Search
CPC ... C07D 405/06; C07D 405/14; A61K 31/505
USPC ......................................................... 514/275
See application file for complete search history.

(56) References Cited

U.S. PATENT DOCUMENTS

| | | | |
|---|---|---|---|
| 4,681,893 A | 7/1987 | Roth et al. | |
| 4,925,852 A | 5/1990 | Kesseler et al. | |

FOREIGN PATENT DOCUMENTS

| | | | |
|---|---|---|---|
| EP | 0409281 | 7/1990 | |
| EP | 0521471 | 1/1991 | |
| EP | 1834944 | 9/2007 | |
| WO | 2005/012246 | 2/2005 | |
| WO | 2005/092867 | 10/2005 | |
| WO | WO 2005/092867 | * 10/2005 | |
| WO | 2006/122644 | 11/2006 | |
| WO | 2010/103318 | 9/2010 | |
| WO | 2010/103319 | 9/2010 | |
| WO | 2010/103320 | 9/2010 | |

OTHER PUBLICATIONS

Baginsky MD, Peter "Should we treat all patients with coronary heart disease or the equivalent with statins?" Current Atherosclerosis Reports 11: 28-35 (2009).

Baker, S. and Tamopolsky, M., "Satin Myopathies: pathophysiologic and clinical perspectives," Clin Invest Med., 24 (5):258-272 (Oct. 2001).
Cancer definition in MedicineNet.com-Sep. 18, 2004.
Clendening and Penn, "Targeting tumor cell metabolism with statins," Oncogene. 31:4967-4978(2012).
Crestor rosuvastatin Calcium "Highlights of Prescribing Information" Dec. 1, 2012.
Haleblian, J., "Characterization of habits and crystalline modifications of solids and their pharmaceutical applications," J Pharm Sci, 64(8): 1269-1288, (Aug. 1975).
Hamelin, B. and Turgeon, J., "Hydrophilicity/ lipophilicity: relevance for the pharmacology and clinical effects of HMG-CoA reductase inhibitiors," Trends in Pharmacological Science 19(1): 26-37, (Jan. 1, 1998).
International Search Report cited in International Application No. PCT/GB2010/050407 mailed May 7, 2010.
International Search Report cited in International Application No. PCT/GB2010/050409 mailed May 3, 2010.
International Search Report cited in International Application No. PCT/GB2010/050408 mailed May 4, 2010.
Klein et. al., "Statin Use and Incident Nuclear Cataract," JAMA. 295(23): 2752-2758 92006).
Krane and Wanner, "Statins, inflammation and kidney disease," Nat. Rev. Nephrol. 7: 385-397 92011).
Lai et. al., "The impact of statin therapy on long-term cardiovascular outcomes in an outpatient cardiology practice," Med. Sci. Monit. 17(12):CR683-686 (2011).
Lee and Park, "Should patients with high cardiovascular risk and an LDL-C concentration below 70 mh/dl be treated with aggressive statin therapy?". Clin. Lipidol. 7(1): 1-4 (2012).
Minder et. al., "Evidence -based use of statins for primary prevention of cardiovascular disease," The American Journal of Medicine. 125: 440-446 (2012).
Office Action for U.S. Appl. No. 13/255,705 dated Dec. 3, 2012.
Office Action for U.S. Appl. No. 13/255,705 dated Jun. 19, 2013.
Souillac, et. al. Characterizations of Delivery Systems, Differential Scanning Calorimetry, pp. 217-218 in the Encyclopedia of Controlled Drug Delivery, 1999 John Wiley & Sons, pp. 212-227.
Tararov, V., et. al., "Synthesis of the chiral side of chain of statins— lactone versus lactol pathway," European Journal of Organic Chemistry, 24:5543-5550, (Dec. 2006).
Vippagunta et. al. Crystalline Solids, Advanced Drug Delivery Reviews, 48 (2001) pp. 3-26.
Wolozin et. al., "Simvastatin is associated with reduced incidence of dementia and parkinson's disese," BMC Medicine. 5(20): 1-11 (2007).

(Continued)

*Primary Examiner* — Valerie Rodriguez-Garcia
(74) *Attorney, Agent, or Firm* — Greenberg Traurig, LLP; Chinh H. Pham; Natalie Salem

(57) ABSTRACT

This invention relates to the discovery of novel rosuvastatin analogs. More specifically, the invention relates to novel rosuvastatin analogs which have utility in treating conditions treatable by the inhibition of HMG-CoA reductase.

26 Claims, 1 Drawing Sheet

(56) References Cited

OTHER PUBLICATIONS

Wong et.al. "HMG-CoA reductase inhibitors and the malignant cell: the statin family of drugs as triggers of tumor-specific apoptosis" Leukemia (2002) 16, 508-519.

Beck et al., "Synthesis and biological activity of new HMG-CoA reductase inhibitors. 1. Lactones of pyridine- and pyrimidine-substituted 3,5-dihydroxy-6-heptenoic (-heptanoic) acids," J. Med. Chem. 33(1):52-60 (1990).

* cited by examiner

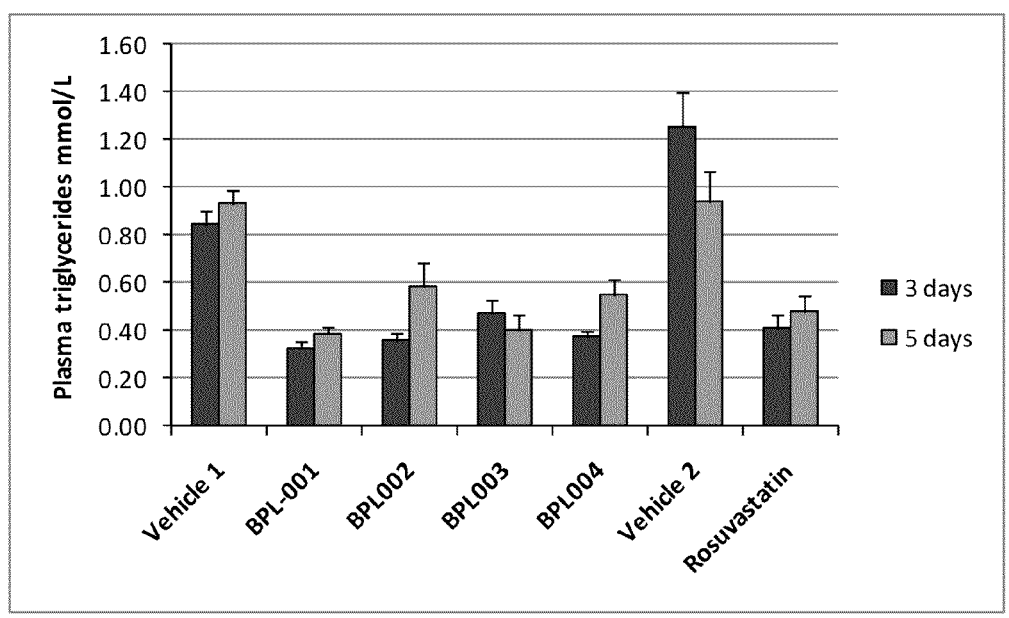

USE OF ROSUVASTATIN LACTOLS AS MEDICAMENTS

This application is a divisional of U.S. patent application Ser. No. 13/255,705, filed Sep. 9, 2011, which is a national phase filing under 35 U.S.C. 371 of International Application No. PCT/GB2010/050409, filed Mar. 10, 2010 and which application claims the benefit of and priority to United Kingdom Patent Application No. GB0904100.5 filed on Mar. 10, 2009, the contents of these applications are herein incorporated by reference in their entirety.

The present invention relates to rosuvastatin lactols. In particular, the present invention relates to the use of rosuvastatin lactols in the manufacture of a medicament for treating certain conditions. Conditions that are treatable using the compounds of the present invention include conditions which are modulated by the enzyme 3-hydroxy-3-methylglutaryl-coenzyme A reductase (HMG-CoA reductase). Inhibition of the enzyme therefore represents a viable therapy for a number of diseases. The compounds used in the invention are 6-(3- or 4-carboxamido-substituted pyrrol-1-yl)-4-hyroxy-3,5-dihydro-pyran-2-ol derivatives.

Rosuvastatin, 7-[4-(4-fluorophenyl)-6-(1-methylethyl)-2-(methyl-methylsulfonyl-amino)-pyrimidin-5-yl]-3,5-dihydroxy-hept-6-enoic acid, and its use in the inhibition of the biosynthesis of cholesterol was first disclosed in EP 0521471. Rosuvastatin is a potent inhibitor of HMG-CoA enzyme.

Clin Invest Med, Volume 24, No 5, p 258-72, 2001 (Baker and Tamopolsky) discloses that whilst statins having an open, hydroxy acid conformation are active, the lactone, closed-ring analogue is inactive. Hepatic hydrolysis at alkaline pH decyclises and hence activates the lactone prodrugs lovastatin and simvastatin in vivo. However, one problem with such compounds is that extensive first path metabolism leads to rapid clearance of these statins.

Similarly, Trends in Pharmacological Sciences, Volume 19, Issue 1, 1 Jan. 1998, Pages 26-37 discloses that the inactive lactones must be metabolised to their corresponding open hydroxy acid forms in order to inhibit HMG-CoA reductase in the manner that rosuvastatin does.

The lactone form, and also the ring opened active form, may suffer problems in terms of stability over an extended period of time. This represents a significant problem during manufacture of an active principal or during extended storage of the same in a pharmacy. For example, loss of the hydroxy group in a dehydration reaction may occur. The resulting decomposition product may have a double bond that is conjugated with the lactone carbonyl group and this will tend to favour the potential decomposition product. Equally, in the ring opened form, one of the possible decomposition products could also have a conjugated double bond with the acid carbonyl group.

It is therefore an aim of the present invention to provide compounds capable of inhibiting HMG-CoA reductase. Rosuvastatin is a very potent inhibitor of HMG-CoA reductase. It is also therefore an aim of the present invention to provide compounds capable of inhibiting HMG-CoA reductase which have an IC50 value comparable to or better than that of rosuvastatin. Ideally, these compounds will have good stability and bioavailability relative to rosuvastatin. It is thus an aim to provide compounds having improved stability. Ideally, the compounds will have an extended shelf-life. It is thus an aim of the present invention to provide compounds capable of inhibiting HMG-CoA reductase which have increased half-life. It is thus an aim of the present invention to provide further compounds capable of inhibiting HMG-CoA reductase and having improved bioavailability. It is also an aim of the present invention to provide compounds capable of inhibiting HMG-CoA reductase and increasing promotion of high density lipoprotein (HDL). It is also an aim of the present invention to provide compounds capable of reducing low density lipoprotein (LDL) and increasing promotion of high density lipoprotein (HDL). Specifically, it is an aim of the present invention to provide compounds capable of reducing low density lipoprotein (LDL) and increasing promotion of high density lipoprotein (HDL) by more than 10%, preferably up to 15% or higher. The invention thus seeks to provide therapies for inhibiting cholesterol biosynthesis. The invention also aims to treat a range of diseases in which cholesterol formation is inhibited.

This invention provides compounds that achieve one or more of the above aims.

According to one aspect, the present invention provides a use of a compound of Formula I and pharmaceutically acceptable salts and solvates thereof:

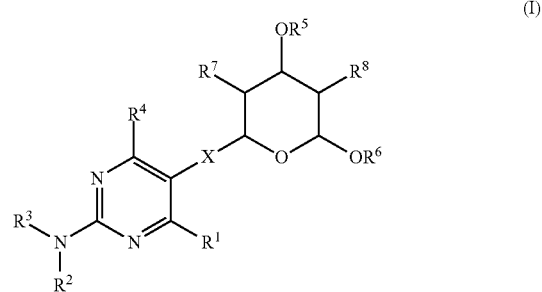

(I)

in the manufacture of a medicament for treating a condition treatable by the inhibition of the enzyme 3-hydroxy-3-methylglutaryl-coenzyme A reductase (HMG-CoA reductase), wherein:

$R^1$ and $R^4$ are independently selected from the group comprising: hydrogen, halo, $C_{1-6}$ alkyl, $C_{2-6}$ alkenyl, $C_{3-6}$ cycloalkyl, aryl, $C_{1-4}$ alkyl aryl, heterocyclyl, and $C_{1-4}$ alkyl heteroaryl;

$R^2$ is —$S(O)_2R^9$ wherein $R^9$ is $C_{1-6}$ alkyl, $C_{3-6}$ cycloalkyl, $C_{1-6}$ alkyl aryl or aryl;

$R^3$ is hydrogen, $C_{1-6}$ alkyl, $C_{2-6}$ alkenyl, $C_{3-6}$ cycloalkyl or aryl;

$R^5$ and $R^6$ are independently selected from the group comprising: hydrogen, $C_{1-6}$ alkyl, $C_{1-6}$ haloalkyl, $C_{2-6}$ alkenyl, $C_{3-6}$ cycloalkyl, aryl, $C_{1-6}$ alkyl aryl, $C_{1-6}$ alkanoyl aryl, heteroaryl, $C_{1-6}$ alkanoyl heteroaryl and $C_{1-6}$ alkyl heteroaryl; provided always that both $R^5$ and $R^6$ are not hydrogen;

$R^7$ and $R^8$ are independently selected from the group comprising: H, $C_{1-4}$ alkyl and halo;

X is —$(CR^aR^b)_m(CR^a=CR^b)_n(CR^aR^b)_o$ where $R^a$ and $R^b$ are independently selected from the group comprising: H, methyl, ethyl and halo and m, n, and o are independently 0, 1, 2, or 3 provided that m+n+o is not more than 3; and wherein each of the above groups $R^1$ to $R^9$ may, where chemically possible, be independently optionally substituted by from 1 to 5 groups chosen independently at each occurrence from the groups comprising: halo, $C_{1-3}$ alkyl, halo $C_{1-3}$ alkyl, $C_{1-3}$ alkoxy, $C_{1-3}$ haloalkoxy, hydroxy, and cyano.

Usually conditions that are modulated by HMG-CoA reductase are conditions that would be treated by the inhibition of the enzyme using a compound of the present invention.

According to another aspect, the present invention provides a compound of Formula I and pharmaceutically acceptable salts and solvates thereof:

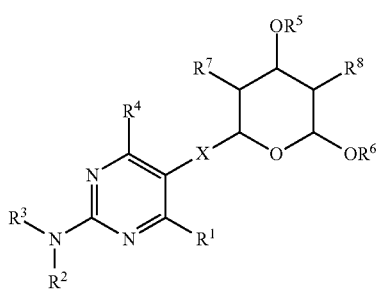

for use in treating a condition treatable by the inhibition of the enzyme 3-hydroxy-3-methylglutaryl-coenzyme A reductase (HMG-CoA reductase) wherein $R^1$-$R^9$, $R^a$, $R^b$, X, m, n and o are as defined above.

According to another aspect, the present invention provides a method of treating a condition treatable by the inhibition of the enzyme 3-hydroxy-3-methylglutaryl-coenzyme A reductase (HMG-CoA reductase) comprising administering an effective amount of a compound of Formula I:

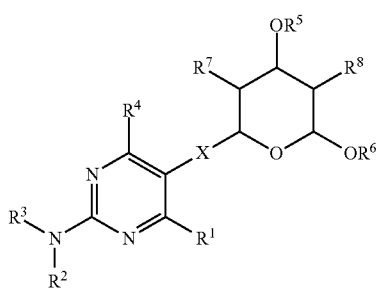

or a pharmaceutically acceptable salt or solvate thereof, wherein $R^1$-$R^9$, $R^a$, $R^b$, X, m, n and o are as defined above.

The compounds of the invention may have activity in their own right or may in certain cases ring open under physiological conditions to corresponding compounds having inhibitory activity.

Reference is made to the accompanying FIGURE (FIG. 1) which illustrates the effect on the level of plasma triglycerides in rats after administration of rosuvastatin (25 mg/kg po) and four rosuvastatin analogues (25 mg/kg).

Pharmaceutically acceptable salts of the compounds of formula (1) include the acid addition and base salts thereof.

Suitable acid addition salts are formed from acids which form non-toxic salts. Examples include the acetate, aspartate, benzoate, besylate, bicarbonate/carbonate, bisulphate/sulphate, borate, camsylate, citrate, edisylate, esylate, formate, fumarate, gluceptate, gluconate, glucuronate, hexafluorophosphate, hibenzate, hydrochloride/chloride, hydrobromide/bromide, hydroiodide/iodide, isethionate, lactate, malate, maleate, malonate, mesylate, methylsulphate, naphthylate, 1,5-naphthalenedisulfonate, 2-napsylate, nicotinate, nitrate, orotate, oxalate, palmitate, pamoate, phosphate/hydrogen phosphate/dihydrogen phosphate, saccharate, stearate, succinate, tartrate, tosylate and trifluoroacetate salts.

Suitable base salts are formed from bases which form non-toxic salts. Examples include the aluminium, arginine, benzathine, calcium, choline, diethylamine, diolamine, glycine, lysine, magnesium, meglumine, olamine, potassium, sodium, tromethamine and zinc salts. Hemisalts of acids and bases may also be formed, for example, hemisulphate and hemicalcium salts. For a review on suitable salts, see "Handbook of Pharmaceutical Salts: Properties, Selection, and Use" by Stahl and Wermuth (Wiley-VCH, Weinheim, Germany, 2002).

Pharmaceutically acceptable salts of compounds of formula (1) may be prepared by one or more of three methods:
(i) by reacting the compound of formula (1) with the desired acid or base;
(ii) by removing an acid- or base-labile protecting group from a suitable precursor of the compound of formula (1) or by ring-opening a suitable cyclic precursor, for example, a lactone or lactam, using the desired acid or base; or
(iii) by converting one salt of the compound of formula (1) to another by reaction with an appropriate acid or base or by means of a suitable ion exchange column.

All three reactions are typically carried out in solution. The resulting salt may precipitate out and be collected by filtration or may be recovered by evaporation of the solvent. The degree of ionisation in the resulting salt may vary from completely ionised to almost non-ionised.

The compounds of the invention may exist in both unsolvated and solvated forms. The term 'solvate' is used herein to describe a molecular complex comprising the compound of the invention and a stoichiometric amount of one or more pharmaceutically acceptable solvent molecules, for example, ethanol. The term 'hydrate' is employed when said solvent is water.

Included within the scope of the invention are complexes such as clathrates, drug-host inclusion complexes wherein, in contrast to the aforementioned solvates, the drug and host are present in stoichiometric or non-stoichiometric amounts. Also included are complexes of the drug containing two or more organic and/or inorganic components which may be in stoichiometric or non-stoichiometric amounts. The resulting complexes may be ionised, partially ionised, or non-ionised. For a review of such complexes, see J Pharm Sci, 64 (8), 1269-1288 by Haleblian (August 1975).

Hereinafter all references to compounds of formula (1) include references to salts, solvates and complexes thereof and to solvates and complexes of salts thereof.

The compounds of the invention include compounds of formula (1) as hereinbefore defined, including all polymorphs and crystal habits thereof, prodrugs and isomers thereof (including optical, geometric and tautomeric isomers) as hereinafter defined and isotopically-labeled compounds of formula (1).

Before purification, the compounds of the present invention may exist as a mixture of enantiomers depending on the synthetic procedure used. For example, the compounds of the present invention may exist as a mixture of enantiomers having a ratio of between 2:1 and 3:1, though they may also occur in other ratios. The enantiomers can be separated by conventional techniques known in the art. Thus the invention covers individual enantiomers as well as mixtures thereof. When the chemical structures disclosed herein includes an '*', it is intended that the compound is a mixture of enantiomers having a ratio of between 2:1 and 3:1.

For some of the steps of the process of preparation of the compounds of formula (1), it may be necessary to protect potential reactive functions that are not wished to react, and to cleave said protecting groups in consequence. In such a case, any compatible protecting radical can be used. In particular methods of protection and deprotection such as those described by T. W. GREENE (Protective Groups in Organic Synthesis, A. Wiley-Interscience Publication, 1981) or by P.

J. Kocienski (Protecting groups, Georg Thieme Verlag, 1994), can be used. All of the above reactions and the preparations of novel starting materials used in the preceding methods are conventional and appropriate reagents and reaction conditions for their performance or preparation as well as procedures for isolating the desired products will be well-known to those skilled in the art with reference to literature precedents and the examples and preparations hereto.

Also, the compounds of formula (1) as well as intermediate for the preparation thereof can be purified according to various well-known methods, such as for example crystallization or chromatography.

In an embodiment, $R^1$ is selected from the group comprising: hydrogen, $C_{1-6}$ alkyl, $C_{2-6}$ alkenyl or $C_{3-6}$ cycloalkyl. In an embodiment, $R^1$ is selected from the group comprising: $C_{2-6}$ alkenyl or $C_{3-6}$ cycloalkyl. In an alternative embodiment, $R^1$ is $C_{1-6}$ alkyl. In an embodiment, $R^1$ is methyl, ethyl, propyl or butyl. In an embodiment, $R^1$ is i-propyl.

In an embodiment, $R^2$ is —$S(O)_2R^9$ wherein $R^9$ is $C_{1-6}$ alkyl. In an embodiment, $R^2$ is —$S(O)_2R^9$ wherein $R^9$ is methyl, ethyl, propyl or butyl. In an embodiment, $R^2$ is —$S(O)_2$Me.

In an embodiment, $R^3$ is selected from the group comprising: hydrogen, $C_{1-6}$ alkyl and $C_{3-6}$ cycloalkyl. In an embodiment, $R^3$ is selected from the group comprising: hydrogen and $C_{1-6}$ alkyl. In an embodiment, $R^3$ is methyl, ethyl or propyl. In an embodiment, $R^3$ is methyl.

In an embodiment, $R^4$ is selected from the group comprising: aryl, $C_{1-4}$ alkyl aryl, heteroaryl and $C_{1-4}$ alkyl heteroaryl, wherein each of the aforementioned groups may be optionally substituted as discussed above in relation to the first aspect. In an embodiment, $R^4$ is selected from the group comprising: aryl and $C_{1-4}$ alkyl aryl. In an embodiment, $R^4$ is aryl. In an embodiment, $R^4$ is phenyl. In an embodiment, $R^4$ is substituted with halo, preferably wherein the halo is fluorine. In an embodiment, $R^4$ is 4-fluorophenyl.

In an embodiment, $R^5$ is selected from the group comprising: hydrogen, $C_{1-6}$ alkyl, aryl, $C_{1-6}$ alkyl aryl, $C_{1-6}$ alkanoyl aryl, heteroaryl, $C_{1-6}$ alkanoyl heteroaryl and $C_{1-6}$ alkyl heteroaryl. In an embodiment, $R^5$ is selected from the group comprising: hydrogen, $C_{1-6}$ alkyl aryl, $C_{1-6}$ alkanoyl aryl, $C_{1-6}$ alkyl heteroaryl and $C_{1-6}$ alkanoyl heteroaryl. In an embodiment, $R^5$ is hydrogen. In an alternative embodiment, $R^5$ is $C_{1-6}$ alkyl aryl, e.g. —$C_1$ alkyl-Ph, —$C_2$ alkyl-Ph, —$C_3$ alkyl-Ph, or —$C_4$ alkyl-Ph. In an embodiment, $R^5$ is benzyl. In an alternative embodiment, $R^5$ is $C_{1-6}$ alkanoyl heteroaryl, e.g. —(C=O)-het, $CH_2$—(C=O)-het or (C=O)—$CH_2$-het (wherein 'het' is heteroaryl). In an embodiment, $R^5$ is $C_{1-6}$ alkanoyl pyridine, e.g. 2-methanoyl pyridine, 3-methanoyl pyridine or 4-methanoyl pyridine, preferably 3-methanoyl pyridine.

In an embodiment, $R^6$ is selected from the group comprising: hydrogen, $C_{1-6}$ alkyl, $C_{1-6}$ haloalkyl, $C_{2-6}$ alkenyl, $C_{3-6}$ cycloalkyl, aryl, $C_{1-6}$ alkyl aryl, heteroaryl and $C_{1-6}$ alkyl heteroaryl. In an embodiment, $R^6$ is $C_{1-6}$ alkyl. In an embodiment, $R^6$ is methyl or ethyl. In another embodiment, $R^6$ is propyl or butyl. In an embodiment, $R^6$ is $C_{1-6}$ haloalkyl, e.g. a $C_{1-6}$ chloroalkyl such as chloromethyl, chloroethyl, chloropropyl or chlorobutyl. In an embodiment, $R^6$ is $C_{2-6}$ alkenyl, e.g. propylene. In an embodiment, $R^6$ is optionally substituted aryl e.g. $C_{1-6}$ alkoxy substituted phenyl or halo substituted phenyl. In a preferred embodiment, $R^6$ is 2,4,6-trifluorophenyl. In a preferred embodiment, $R^6$ is 2,4-dimethoxyphenyl.

In an embodiment, $R^7$ is H.
In an embodiment, $R^8$ is H.

In an embodiment, m=0. In an embodiment, o=0. In an embodiment, n=1. In an embodiment, m=0, n=1 and o=0. In an embodiment, m=1, n=1 and o=0, or m=0, n=1 and o=1.

In an embodiment, $R^a$ is H at each occurrence.
In an embodiment, $R^b$ is H at each occurrence.
In a further embodiment, $R^a$ is H, $R^b$ is H and m=0, n=1 and o=0.

Aryl groups include aromatic ring systems comprising 6, 7, 8, 9, 10, 11, 12, 13, 14, 15 or 16 ring carbon atoms. Aryl groups may consist of a single ring but may include a polycyclic ring system, having two or more rings, at least one of which is aromatic. Aryl groups include: phenyl, naphthyl, fluorenyl, azulenyl, indenyl and anthryl groups.

In an embodiment, the aryl group is phenyl.

Heteroaryl groups include aromatic heterocyclic ring systems having 5, 6, 7, 8, 9, 10, 11, 12, 13, 14, 15 or 16 ring atoms with 1 to 4 heteroatoms independently selected from nitrogen, oxygen and sulfur. The group may be a polycyclic ring system, having two or more rings, at least one of which is aromatic, but is more often monocyclic. Preferred heteroaryl groups are monocyclic groups containing 5 or 6 ring atoms. Heteroaryl groups include: pyrrolyl, pyrazolyl, imidazolyl, pyrazinyl, oxazolyl, isoxazolyl, thiazolyl, furyl, thiophenyl, pyridyl, pyrimidyl, benzimidazolyl, indolyl, isoquinolyl, quinoxalinyl and quinolyl.

In an embodiment, the heteroaryl group is selected from the group comprising: pyridine, pyrimidine, pyrazine, pyrazole, and oxazole. Preferably the heteroaryl group is pyridine.

When one or more of the above groups is optionally substituted, each optional substituent is preferably an independently chosen halo atom. Amongst halo, chloro and fluoro are preferred. Preferably, the halo atoms are the same when there are more than one.

In an embodiment, $R^1$ is $C_{1-4}$ alkyl, preferably i-propyl, and $R^4$ is optionally substituted aryl, preferably 4-fluorophenyl.

In another embodiment, $R^2$ is —$S(O)_2R^9$ wherein $R^9$ is $C_{1-6}$ alkyl, preferably methyl, and $R^3$ is hydrogen or $C_{1-6}$ alkyl, preferably methyl.

In an embodiment, $R^1$ is $C_{1-4}$ alkyl, preferably i-propyl; $R^2$ is —$S(O)_2R^9$ wherein $R^9$ is $C_{1-6}$ alkyl, preferably methyl; $R^3$ is hydrogen or $C_{1-6}$ alkyl, preferably methyl; and $R^4$ is optionally substituted aryl, preferably 4-fluorophenyl.

The relationship between the groups $R^5$ and $R^6$ is important for the activity of the compounds. Thus both $R^5$ and $R^6$ cannot be hydrogen. Similarly, when $R^5$ is hydrogen, $R^6$ ideally should not be an unsubstituted $C_{1-6}$ alkyl group e.g. methyl, ethyl, iso-propyl or tert-butyl. In one embodiment, $R^5$ is not hydrogen. In one embodiment, $R^6$ is not hydrogen.

In another embodiment, $R^5$ is hydrogen and $R^6$ is an optionally substituted aromatic group. In this embodiment, preferably the aromatic group is substituted by between 1 and 5 substituents as recited above. Preferably, the aromatic group is ortho and/or para substituted, preferably ortho and para substituted with 2 or 3 substituents. Preferably the substituents for the aromatic group are halogen (e.g. fluorine or chlorine). Preferably the substituents for the aromatic group are $C_{1-4}$ alkoxy (e.g. methoxy).

In another embodiment, $R^5$ is hydrogen and $R^6$ is a $C_{1-6}$ haloalkyl group. In this embodiment, the haloalkyl group is preferably a chloroalkyl group. The haloalkyl group is preferably haloethyl. A particularly preferred group is —$CH_2CCl_3$.

In another embodiment, $R^5$ is an optionally substituted benzyl and $R^6$ is an optionally substituted $C_{1-6}$alkyl, preferably methyl, propyl, isopropyl, butyl, isobutyl or tertbutyl. In another embodiment, $R^5$ is an optionally substituted benzyl and $R^6$ is an optionally substituted $C_{2-6}$ alkenyl, preferably propylene. In another embodiment, $R^5$ is an optionally substituted benzyl and $R^6$ is a $C_{1-6}$ haloalkyl, preferably 2,2,2-trichlororethyl.
In another embodiment, $R^5$ is a $C_{1-6}$ alkanoyl heteroaryl group and $R^6$ is an optionally substituted $C_{1-6}$alkyl, preferably methyl, ethyl or propyl.
In an embodiment, the compound has a structure selected from:
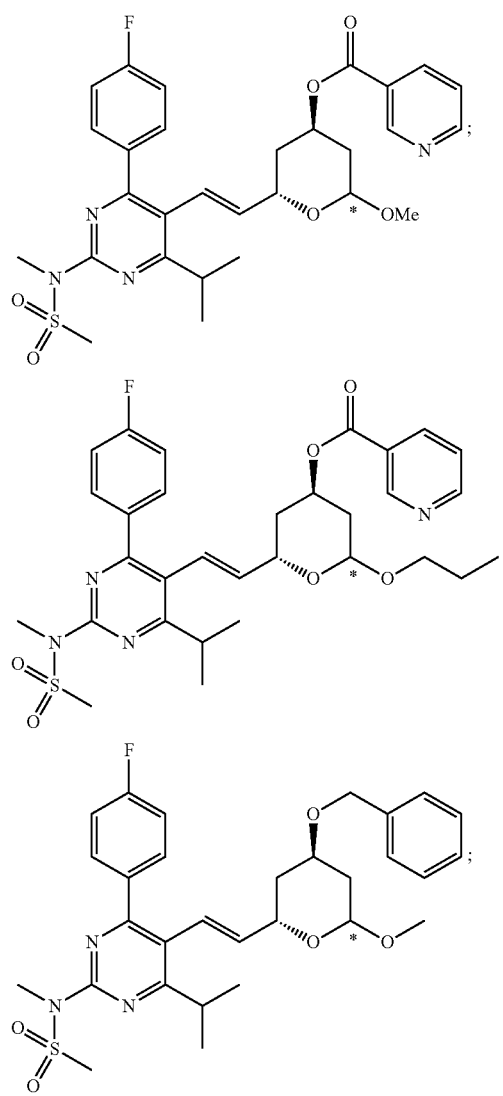
-continued
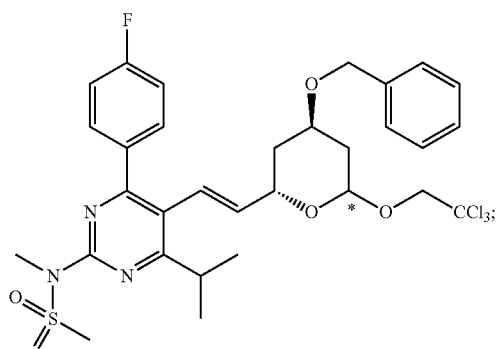
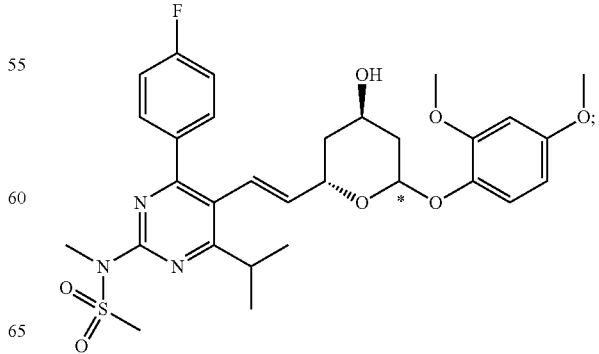

-continued

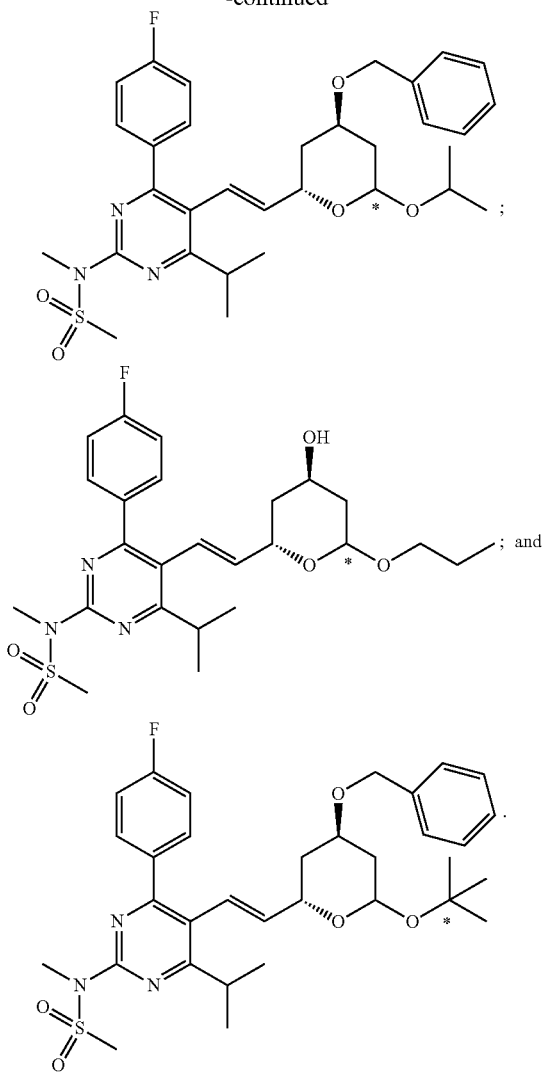

As mentioned above, statins having an open, hydroxy acid conformation are known to have an inhibitory effect on HMG-CoA reductase. It is also known that the lactone, closed-ring analogue of such hydroxy acids are inactive with respect to inhibiting HMG-CoA reductase and that decyclisation of the lactone is necessary to activate the lactone.

However, we have found that functionalised lactols of the present invention have a significant inhibitory effect on HMG-CoA reductase in their own right. This is surprising in view of the fact that these molecules are conformationally constrained in ring closed form.

Examples of conditions that may be treated by the inhibition of HMG-CoA reductase include hypercholesterolemia, atherosclerosis and hyperlipidemia. Statins have been used in the secondary prevention of cardiovascular disease, or in the primary prevention of cardiovascular disease when the risk for cardiovascular disease is significantly raised. It is therefore expected that the compounds of the present invention will have utility in the treatment or prevention of cardiovascular diseases due to their inhibitory activity. Example cardiovascular diseases which may be treatable by the compounds of the present invention include: coronary heart disease, myocardial infarction, stroke and peripheral artery disease. In addition, these compounds may also have a beneficial effect in the treatment of inflammation, dementia, cancer, nuclear cataracts, diabetes and hypertension.

The conditions that may be treated by the inhibition of HMG-CoA reductase may be a condition of the human or animal body. These compounds are intended in particular for human patients.

Processes for the manufacture of the compounds of the present invention are disclosed in WO2005/092867, in particular, in the examples. The disclosure of WO2005/092867 insofar as the synthetic procedures are concerned forms part of the disclosure of the present invention. In the interests of brevity, the details of these synthetic procedures is not reproduced here but it is intended that this subject matter is specifically incorporated into the disclosure of this document by reference.

The present invention also includes the synthesis of all pharmaceutically acceptable isotopically-labelled compounds of formula (I) wherein one or more atoms are replaced by atoms having the same atomic number, but an atomic mass or mass number different from the atomic mass or mass number usually found in nature.

Examples of isotopes suitable for inclusion in the compounds of the invention include isotopes of hydrogen, such as $^2$H and $^3$H, carbon, such as $^{11}$C, $^{13}$C and $^{14}$C, chlorine, such as $^{36}$Cl, fluorine, such as $^{18}$F, iodine, such as $^{123}$I and $^{125}$I, nitrogen, such as $^{13}$N and $^{15}$N, oxygen, such as $^{15}$O, $^{17}$O and $^{18}$O, phosphorus, such as $^{32}$P, and sulphur, such as $^{35}$S.

Certain isotopically-labelled compounds, for example, those incorporating a radioactive isotope, are useful in drug and/or substrate tissue distribution studies. The radioactive isotopes tritium, i.e. $^3$H, and carbon-14, i.e. $^{14}$C, are particularly useful for this purpose in view of their ease of incorporation and ready means of detection.

Substitution with heavier isotopes such as deuterium, i.e. $^2$H, may afford certain therapeutic advantages resulting from greater metabolic stability, for example, increased in vivo half-life or reduced dosage requirements, and hence may be preferred in some circumstances.

Substitution with positron emitting isotopes, such as $^{11}$C, $^{18}$F, $^{15}$O and $^{13}$N, can be useful in Positron Emission Topography (PET) studies for examining substrate receptor occupancy.

Isotopically-labelled compounds can generally be prepared by conventional techniques known to those skilled in the art or by processes analogous to those described using an appropriate isotopically-labelled reagent in place of the non-labelled reagent previously employed.

Throughout the description and claims of this specification, the words "comprise" and "contain" and variations of the words, for example "comprising" and "comprises", means "including but not limited to", and is not intended to (and does not) exclude other moieties, additives, components, integers or steps.

Throughout the description and claims of this specification, the singular encompasses the plural unless the context otherwise requires. In particular, where the indefinite article is used, the specification is to be understood as contemplating plurality as well as singularity, unless the context requires otherwise.

Features, integers, characteristics, compounds, chemical moieties or groups described in conjunction with a particular aspect, embodiment or example of the invention are to be understood to be applicable to any other aspect, embodiment or example described herein unless incompatible therewith.

General Procedure

All assays were carried out in a reaction buffer containing 100 nM K$_x$PO$_4$ at pH 7.2, 1 mM EDTA, 500 mM KCl and 1 mg/ml BSA. The concentrations of NADPH and HMG-CoA were both 200 μM. The enzyme concentration used is unknown although this concentration is 10-fold lower than that of the stock solution purchased. Inhibitors were dissolved in 75% DMSO. Where inhibitors were found to be insoluble or only partly soluble in 75% DMSO, 100% DMSO was used. Reactions were activated by the addition of enzyme and agitated for 12 seconds following the addition. Absorbance readings were then taken every 20 seconds for 600 seconds. In initial tests the concentration of each inhibitor was set at 50 nM to identify which compounds were the better inhibitors, compared to the known Pravastatin inhibitor. After these were identified, assays were carried out varying their concentrations from 0 nM to 50 nM allowing IC50 values to be calculated.

EXAMPLE 1

The following procedure was followed using a HMG-CoA Reductase assay kit obtained from Sigma-Aldrich (catalogue number CS1090). The assay is based on the spectrophotometric measurement of the decrease in absorbance at 340 nm of NADPH in solution. A decrease in absorbance is caused by the oxidation of NADPH by the catalytic subunit of HMGR in the presence of the substrate HMG-CoA. Effective inhibition of the HMG-CoA leads to a reduction in oxidation of NADPH which in turn leads to a smaller reduction in the absorbance at 340 nm over time. This is illustrated in the following reaction scheme:

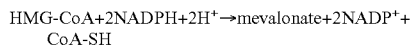

HMG-CoA+2NADPH+2H$^+$→mevalonate+2NADP$^+$+CoA-SH

Compounds showing the best inhibitory action are those which reduce the absorbance least.

Preparation of the Assay Solution

Ultrapure water (17 MΩ-cm or equivalent was used for the preparation of reagents and throughout the procedure.

First, an assay buffer solution was prepared using the following method: 0.2 ml of assay buffer, 5× (catalogue number A5981) was diluted with 0.8 ml of ultrapure water. The resulting buffer solution was kept on ice or stored at −20° C. for further use.

Next, 25 mg of NADPH (catalogue number N6505) was reconstituted with 1.5 ml of the buffer solution. The reconstituted NADPH was stored in working aliquots at −20° C.

The HMG-CoA substrate solution (catalogue number S7447), HMG-CoA reductase (catalogue number H8789) and inhibitor solution (e.g. pravastatin, catalogue number I5909) were kept on ice throughout the procedure.

1. Before beginning, the spectrophotometer was set at 37° C. and 340 nm, with a kinetic programme: 1 ml sample, read every 20 seconds for up to 10 minutes.
2. The appropriate volumes of the reaction solutions were added according to Table 1 (1 ml assay).

TABLE 1

Reaction volumes for 1 ml samples

| Sample | 1× Assay buffer | Test compound/ Pravastatin | NADPH | HMG-CoA | HGMG |
|---|---|---|---|---|---|
| Blank | 920 μl | — | 20 μl | 60 μl | — |
| Activity | 915 μl | — | 20 μl | 60 μl | 5 μl |
| Inhibition | 910 μl | 5 μl | 20 μl | 60 μl | 5 μl |

The reagents were added to the reaction in the following order:
  a. Add a buffer to all samples.
  b. Add the inhibitor (test compound/Pravastatin) to the inhibition sample.
  c. Add the reconstituted NADPH to all samples.
  d. Add Substrate Solution (HMG-CoA) to all samples.
  e. Add HMG-CoA Reductase (HMGR) to the Activity and Inhibition samples.
  f. Mix the samples thoroughly.
3. The kinetics programme was started immediately. The activity of the product was calculated according to the following equation:

$$\text{Units/mgP} = \frac{(\Delta A_{340}/\min_{sample} - \Delta A_{340}/\min_{control}) \times TV}{12.44 \times V \times 0.6 \times LP}$$

where:
12.44=$\epsilon^{mM}$—the extinction coefficient for NADPH at 340 nm is 6.22 mM$^{-1}$ cm$^{-1}$. 12.44 represents the 2 NADPH consumed in the reaction.
TV=total volume of the reaction in ml (1 ml for cuvettes)
V=volume of enzyme used in the assay (ml)
0.6=enzyme concentration in mg-protein (mgP0/ml (0.55-0.65 mgP/ml)
LP=light path in cm (1 for cuvettes).

EXAMPLE 2

The following table provides IC50 values for particular rosuvastatin compounds of the present invention.

| Compound Structure | IC$_{50}$ (nM) |
|---|---|
| Rosuvastatin calcium salt | 4 |
| [structure 1] | <1 |
| [structure 2] | 8 |

| Compound Structure | IC$_{50}$ (nM) | Compound Structure | IC$_{50}$ (nM) |
|---|---|---|---|
| (structure) | 1 | (structure) | 2 |
| (structure) | 22 | (structure) | 1 |
| (structure) | 4 | (structure) | 2 |
| (structure) | 3 | (structure) | 2 |

-continued

| Compound Structure | IC$_{50}$ (nM) |
|---|---|
| (4-fluorophenyl pyrimidine rosuvastatin lactol n-propyl acetal with N-methyl methanesulfonamide) | 10 |

EXAMPLE 3

The following example demonstrates the efficacy of the compounds of the invention. The Example demonstrates the effect of 3 or 5 days BID treatment with four rosuvastatin compounds of the present invention and rosuvastatin (all at 25 mg/kg po) on rat plasma triglyceride levels 16 hours after the last treatment dose. The measurement of the change in rat plasma triglyceride levels is considered to be a fair test for determining HMG CoA reductase activity.

112 male SD rats (Harlan) were housed in groups of 6 under a 12 h light dark cycle (lights on 07.00 h) with free access to food (normal laboratory chow) and water. Animals between 148-183 g were allocated to treatment groups of 8 balanced by body weight and treatments were balanced across cages.

Four rosuvastatin analogues were made up in 10% PEG300/10% cremophor/80% methyl cellulose (0.5%) (vehicle 1) to make a 5 mg/mL solution. The rosuvastatin compounds used were:

Rosuvastatin Lactol n-propyl acetal (diastereomeric ratio 2/1) (BPL001); Rosuvastatin lactol n-propyl acetal nicotinoyl ester (diastereomeric ratio 2/1) (BPL002); Rosuvastatin lactol iso-propyl acetal benzyl ether (BPL003); and Rosuvastatin lactol methyl acetal nicotinoyl ester (diastereomeric ratio 2/1) (BPL004).

Rosuvastatin was formulated in 0.5% Tween in 0.5% methyl cellulose (vehicle 2) at 5 mg/kg as a suspension.

Rats were orally dosed with vehicle 1, one of the four rosuvastatin analogues in vehicle 1 (25 mg/kg), vehicle 2 or rosuvastatin in vehicle 2 (25 mg/kg po), BID for 3 or 5 days.

Sixteen hours after the last treatment, terminal plasma samples were taken, stored at −20° C., and transported on dry ice for analysis of triglyceride levels.

Data for each time-point were analysed by 1-way ANOVA and post-hoc Dunnett's test.

The results are provided in FIG. 1 from which it can be deduced that administration of rosuvastatin (25 mg/kg po) BID for 3 or 5 days causes a marked reduction in plasma triglycerides. All four rosuvastatin analogues also significantly reduced plasma triglycerides after both 3 and 5 days BID treatment. All animals tolerated the rosuvastatin treatments well and there was no evidence of any adverse events.

The magnitude of the effect of the rosuvastatin analogues was equivalent to that of rosuvastatin.

The invention claimed is:

1. A method of treating a condition comprising: administering an effective amount of a compound of Formula I (I)

or pharmaceutically acceptable salts or solvates thereof to inhibit the enzyme 3-hydroxy-3-methylglutaryl-coenzyme A reductase (HMG-CoA reductase),
wherein the condition is selected from the group consisting of: hypercholesterolemia, atherosclerosis, hyperlipidemia, coronary heart disease, myocardial infarction, stroke, and peripheral artery disease,
further wherein:
$R^1$ and $R^4$ are independently selected from the group consisting of: hydrogen, halo, $C_{1-6}$ alkyl, $C_{2-6}$ alkenyl, $C_{3-6}$ cycloalkyl, aryl, $C_{1-4}$ alkyl aryl, heterocyclyl, and $C_{1-4}$ alkyl heteroaryl;
$R^2$ is —S(O)$_2$R$^9$ wherein $R^9$ is $C_{1-6}$ alkyl, $C_{3-6}$ cycloalkyl, $C_{1-6}$ alkyl aryl or aryl;
$R^3$ is hydrogen, $C_{1-6}$ alkyl, $C_{2-6}$ alkenyl, $C_{3-6}$ cycloalkyl or aryl;
$R^5$ and $R^6$ are independently selected from the group consisting of: hydrogen, $C_{1-6}$ alkyl, $C_{1-6}$ haloalkyl, $C_{2-6}$ alkenyl, $C_{3-6}$ cycloalkyl, aryl, $C_{1-6}$ alkyl aryl, $C_{1-6}$ alkanoyl aryl, heteroaryl, $C_{1-6}$ alkanoyl heteroaryl and $C_{1-6}$ alkyl heteroaryl; provided always that both $R^5$ and $R^6$ are not hydrogen;
$R^7$ and $R^8$ are independently selected from the group consisting of: H, $C_{1-4}$ alkyl and halo;
X is —(CR$^a$R$^b$)$_m$(CR$^a$=CR$^b$)$_n$(CR$^a$R$^b$)$_o$ where R$^a$ and R$^b$ are independently selected from the group consisting of: H, methyl, ethyl and halo and m, n, and o are independently 0, 1, 2, or 3 provided that m+n+o is not more than 3; and wherein each of the above groups $R^1$ to $R^9$ may, where chemically possible, be independently optionally substituted by from 1 to 5 groups chosen independently at each occurrence from the group consisting of: halo, $C_{1-3}$ alkyl, halo $C_{1-3}$ alkyl, $C_{1-3}$ alkoxy, $C_{1-3}$ haloalkoxy, hydroxy, and cyano.

2. The method of claim 1 wherein the condition is selected from the group consisting of: hypercholesterolemia, atherosclerosis, hyperlipidemia, coronary heart disease, myocardial infarction, and peripheral artery disease.

3. The method of claim 1 wherein the condition is selected from the group consisting of: hypercholesterolemia, atherosclerosis and hyperlipidemia.

4. The method of claim 1, wherein $R^1$ is $C_{1-6}$ alkyl.

5. The method of claim 1, wherein $R^9$ is $C_{1-6}$ alkyl.

6. The method of claim 1, wherein $R^3$ is hydrogen or $C_{1-6}$ alkyl.

7. The method of claim 1, wherein $R^4$ is optionally substituted aryl.

8. The method of claim 1, wherein $R^1$ is i-propyl, $R^2$ is —S(O)$_2$Me, $R^3$ is methyl and $R^4$ is 4-fluorophenyl.

9. The method of claim 1, wherein $R^5$ is selected from the group consisting of: hydrogen, $C_{1-6}$ alkyl, aryl, $C_{1-6}$ alkyl aryl, $C_{1-6}$ alkanoyl aryl, heteroaryl, $C_{1-6}$ alkanoyl heteroaryl and $C_{1-6}$ alkyl heteroaryl.

10. The method of claim 9, wherein $R^5$ is hydrogen.

11. The method of claim 9, wherein $R^5$ is selected from the group consisting of: —$C_1$ alkyl-Ph, —$C_2$ alkyl-Ph, —$C_3$ alkyl-Ph, and —$C_4$ alkyl-Ph.

12. The method of claim 11, wherein $R^5$ is benzyl.

13. The method of claim 9, wherein $R^5$ is $C_{1-6}$ alkanoyl pyridine.

14. The method of claim 13, wherein $R^5$ is 3-methanoyl pyridine.

15. The method claim 1, wherein $R^6$ is selected from the group consisting of: hydrogen, $C_{1-6}$ alkyl, $C_{1-6}$ haloalkyl, $C_{2-6}$ alkenyl, $C_{3-6}$ cycloalkyl, aryl, $C_{1-6}$ alkyl aryl, heteroaryl and $C_{1-6}$ alkyl heteroaryl.

16. The method of claim 15, wherein $R^6$ is selected from the group consisting of: $C_{1-6}$ alkyl, $C_{1-6}$ halo alkyl and $C_{2-6}$ alkenyl.

17. The method of claim 16 wherein $R^6$ is selected from the group consisting of: methyl, ethyl, propyl, butyl, chloromethyl, chloroethyl, chloropropyl, chlorobutyl and propylene.

18. The method of claim 15, wherein $R^6$ is optionally substituted aryl.

19. The method of claim 18, wherein $R^6$ is selected from the group consisting of: $C_{1-6}$ alkoxy substituted phenyl and halo substituted phenyl.

20. The method of claim 19, wherein $R^6$ is selected from the group consisting of: 2,4,6-trifluorophenyl and 2,4-dimethoxyphenyl.

21. The method of claim 1, wherein $R^5$ is hydrogen and $R^6$ is an optionally substituted aryl group.

22. The method of claim 1, wherein $R^5$ is an optionally substituted benzyl and $R^6$ is an optionally substituted $C_{1-6}$ alkyl, an optionally substituted $C_{2-6}$ alkenyl or a $C_{1-6}$ haloalkyl.

23. The method of claim 1, wherein $R^5$ is a $C_{1-6}$ alkanoyl heteroaryl and $R^6$ is an optionally substituted $C_{1-6}$ alkyl.

24. The method of claim 1, wherein $R^7$ is H and $R^8$ is H.

25. The method of claim 1, wherein $R^a$ is H, $R^b$ is H and m=0, n=1 and o=0.

26. The method of claim 1 wherein in the step of administering the compound has a structure selected from:

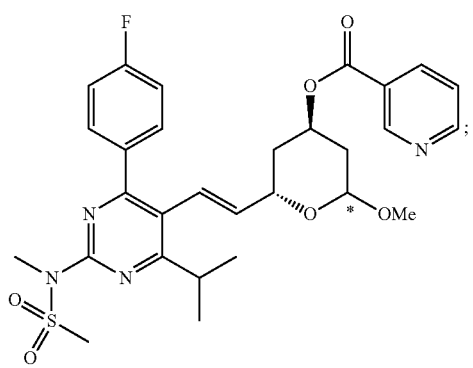

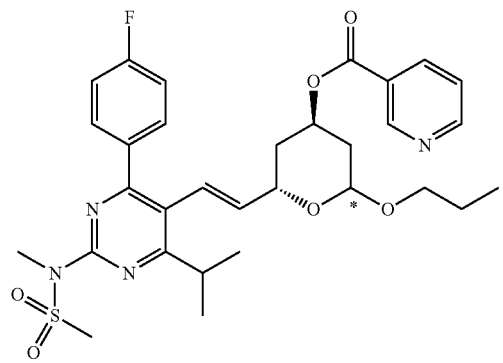

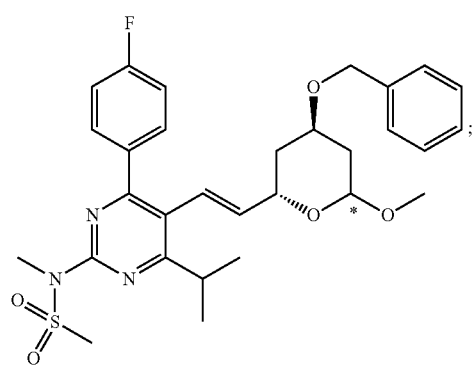

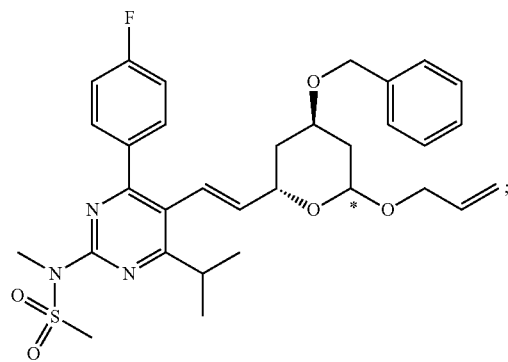

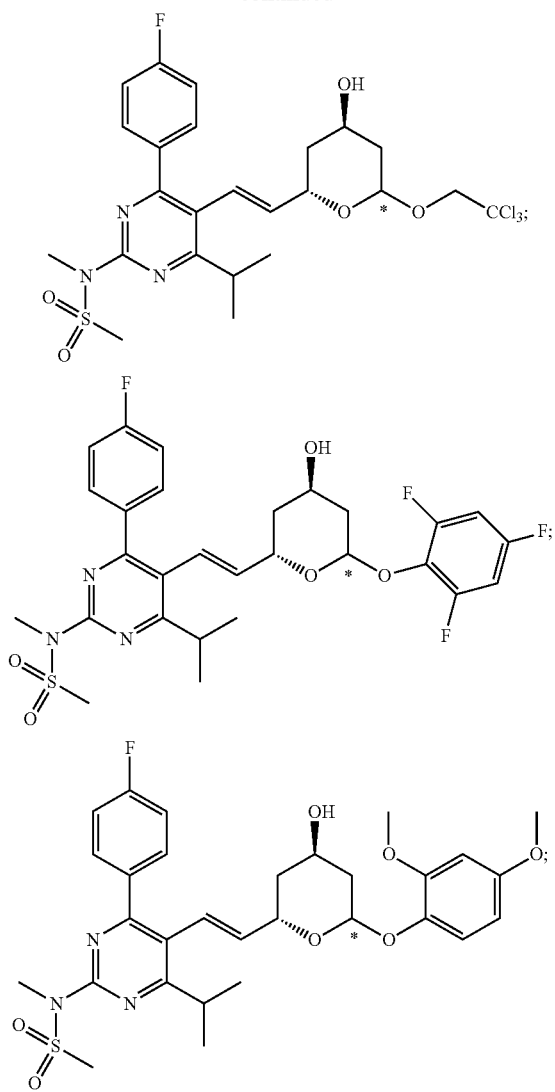
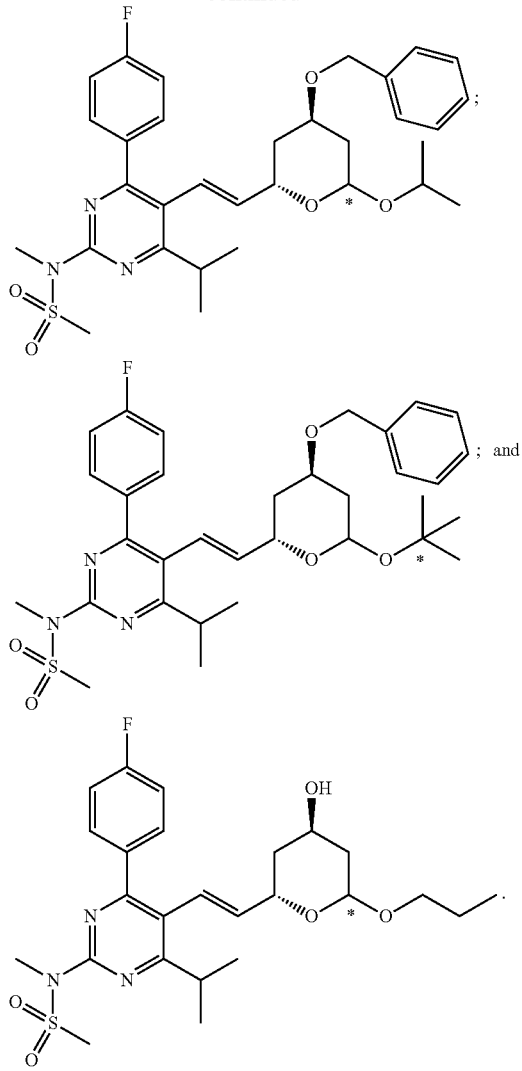
* * * * *